United States Patent [19]

Del Bon

[11] 4,381,009
[45] Apr. 26, 1983

[54] HAND-HELD DEVICE FOR THE LOCAL HEAT-TREATMENT OF THE SKIN

[76] Inventor: Franco Del Bon, 139 Feldstrasse, 4663 Aarburg, Switzerland

[21] Appl. No.: 228,937

[22] Filed: Jan. 28, 1981

[30] Foreign Application Priority Data

Jan. 28, 1980 [CH] Switzerland .................. 654/80-8

[51] Int. Cl.³ ............................................. A61F 7/00
[52] U.S. Cl. ................................. 128/399; 219/241
[58] Field of Search .................. 128/399, 401, 24.1, 128/254, 635; 219/227, 228, 241, 501

[56] References Cited

U.S. PATENT DOCUMENTS

| | | | |
|---|---|---|---|
| 3,308,271 | 3/1967 | Hilbiber | 219/501 |
| 3,320,407 | 5/1967 | Holmes | 219/501 |
| 3,450,863 | 6/1969 | Scholl | 219/501 |
| 4,142,529 | 3/1979 | Latenser et al. | 128/401 |
| 4,227,535 | 10/1980 | Connor | 128/401 |
| 4,290,431 | 9/1981 | Herbert et al. | 128/635 |

FOREIGN PATENT DOCUMENTS 836839 7/1949 Fed. Rep. of Germany ..... 128/24.1
2547949 4/1977 Fed. Rep. of Germany ...... 128/399

*Primary Examiner*—Lee S. Cohen
*Attorney, Agent, or Firm*—Heinrich W. Herzfeld

[57] ABSTRACT

A hand-held device for the local heat treatment of a patient's skin comprises a casing composed of a lower treatment part having a bottom wall with an external treatment face, and an upper handle part, and an electric heating unit in the treatment part comprising a power transistor with a cooling vane and a heat sensor, the cooling vane and the heat sensor being in heat transfer contact with the interior surface of the bottom wall, and an electric circuit unit inside the treatment part for controlling electric current flow through the power transistor depending on temperature variations detected in the bottom wall by the heat sensor. The circuit is fed low voltage direct current from a source therefor.

4 Claims, 8 Drawing Figures

THERMOGRAPH

DARK SKIN ZONES  COOL  POOR BLOOD-FLOW THROUGH SKIN
LIGHT SKIN ZONES  WARM  GOOD BLOOD-FLOW THROUGH SKIN

HAND-HELD DEVICE FOR THE LOCAL HEAT-TREATMENT OF THE SKIN

BACKGROUND OF THE INVENTION

This invention relates to a hand-held device for the local heat treatment of the skin, in particular a facial skin portion, with the aid of an electrically heatable treatment surface which can be brought into contact with the skin.

It is well-known that the local application of heat to a portion of the skin, e.g. of the face of a patient leads to an active hyperemia with capillaroscopically detectable widening of the small vessels of the skin, especially of the superficial plexus, connected with a strong acceleration of local blood flow due to the release of acetyl choline.

This hyperemia affords:

(a) an increase of absorption. The acceleration of the velocity of blood flow is accompanied by an increase of the lymphatic flow. Thereby products of normal digestion and pathological secretions are more rapidly transported away from a diseased location. Moreover, substances brought into contact with the outer surface of the skin are more rapidly transported away, once they have reached the corium because the concentration gradient between the corium and the blood is larger in the hyperemic skin;

(b) an antibacterial effect;

(c) an improved feeding of the tissues; and finally (d) an analgesic effect.

Transportation of a substance through the horny layer of the skin, which layer due to its barrier functions constitutes the main obstacle to the penetration of substances from the outside through the skin, increases with an increase of skin temperature. The increase of the permeability constant with increasing temperature is considerably greater than the increase of the said constant by hydration. There are two reasons for this effect, namely the increase of the activation energy of the molecules of a penetrating substance (increased molecular motion) and the softening of the lipids in the horny layer by increased temperature.

Known devices containing the initially described electrically heatable treatment surface for heat treating the skin as well as a thermostat for switching on and off an electrical heating element suffer from the drawback that the temperature of the treatment surface is subject to larger fluctuations in spite of the control of electrical heating. On the one hand, this cause a danger of overheating which can cause local burns in particular in sensitive parts of the face, when the temperature rises noticeably above 40° C. On the other hand, there is the drawback of excessive cooling which means a loss of time before the device can again be used effectively, namely until the temperature of the treatment surface has risen again to the desired approximately 40° C., a fact which must be determined, for instance, by touching the treatment surface with a finger. Moreover, the known devices are usually unwieldy and difficult to use on strongly curved portions of a patient's body.

OBJECTS AND SUMMARY OF THE INVENTION

It is therefore an object of the invention to provide a device of the initially described type in which the temperature of the treatment surface does only deviate slightly from a desired value during the use of the device and in intervals between two periods of applications, and will quickly reach this desired temperature value; it is another object of the invention to provide a device having the foregoing advantageous features which is of a shape permitting it to be easily held in one hand of the operator and will facilitate a massaging treatment of all parts of a patient's body, and in particular all parts of the patient's face, with the heated treatment surface of the device.

These objects are attained, in accordance with the invention, by a device of the initially described type which comprises, in combination, a casing having a bottom wall, the outer surface of which cntains the above-mentioned treatment face; a handle part which is connected to the casing outside of the bottom wall of the latter; as well as an electric heating unit in the interior of the casing which unit comprises (i) as heating element a power transistor having a cooling vane, and a heat sensor unit for controlling heating of the treatment face of the transistor; the cooling vane of the power transistor and the heat sensor unit being arranged on the inner surface of the bottom wall of the casing; and (ii) an electric circuit disposed in the interior of the casing which circuit is adapted for controlling electric current flow in the power transistor depending on any temperature variations of the bottom wall which are detected by the heat sensor unit;

the said electric circuit being connected with the power transistor and the heat sensor unit and comprising connecting means for connecting the circuit with a source of low-voltage direct current.

Preferably, the cooling vane can be made integral with a hull encapsulating the power transistor, and is preferably of flat shape, being in contact with the inner side of the bottom wall of the casing. The heat sensor unit consists preferably of a cold conductor as heat sensor and a variable resistor associated therewith.

The handle part of the device according to the invention can be concavely vaulted and connected detachably with the treatment part. Preferably the handle part is hollow and contains a connecting lead by way of which the circuitry is connected to a source of low voltage direct current.

The casing of the treatment part can have a rounded rim about its bottom wall and can be open on a side spaced with regard to the bottom wall and preferably opposite the latter. It can be equipped with means for fastening it to a frontal face of the handle part which frontal face contains an opening. The fastening means can be, e.g. a threading or a bayonet-connection or a snap-on connection by means of which the handle part is connected to the casing of the treatment part.

The upper end of the handle part can have the shape of a flattened face so that it can be a supporting surface on which the device can stand when not used so that the treatment face of the casing will be directed upwardly.

Preferably, the circuit will comprise a controlled transistor for controlling the flow of electric current through the power transistor; the collector of the control transistor preferably receives direct current via a resistor and is conductivity connected with the base of the power transistor. Furthermore, the electronic circuit can comprise advantageously a voltage divider consisting of two resistors connected with one another in series. One of these two resistors is a fixed resistor while the other resistor can be the above-mentioned variable resistor associated with the heat sensor, the contact post between the two resistors of the voltage divider being connected with the base of the power transistor.

Furthermore, the entire electronic circuit can comprise a connecting unit which is located at least partially outside the casing of the heat-treatment device. This connecting unit can be connected to the city main and comprises, for this purpose, a step-down transformer for transforming the main voltage, the secondary windings of this transformer and a rectifying unit associated therewith serving as the low-voltage direct current source, while its primary windings can be connected in a conventional manner, preferably by means of a plug, to the main.

From this direct current source the power transistor as well as the control transistor and optionally also the voltage divider can be supplied with low voltage direct current; in the latter case, the voltage divider is preferably connected to the low voltage direct current source, i.e., the secondary windings of a step-down transformer, via a voltage-limiting unit. The latter unit can comprise a Z-diode, connected in parallel with the voltage divider, and a voltage-limiting resistor and the low voltage direct current source.

The collector of the control transistor can be connected via a fixed resistor with one post of the low voltage direct current source which is preferably the same post to which the limiting resistor of the voltage limiting unit is connected, while, preferably, the two emitters, of the power transistor and of the control transistor, are connected to that post of the low voltage direct current source to which there is also connected the variable transistor of the heat sensor unit.

A current-limiting resistor can be provided between the emitter of the power transistor and the low voltage direct current source.

The circuit unit can also comprise as a printed circuit a plate of electrically insulating material, and this plate together with the power transistor and the heat sensor unit can be embedded in an insoluble plastic resin, in order to prevent the circuitry from being copied, removal of the resin leading normally to a destruction of the circuit.

The step-down transformer which can be plugged into the main, is preferably connected with the circuit unit via a resiliently coiled cable which is introduced from the outside through an opening in the sidewall of the handle part into the hollow interior of the latter.

Wherever possible, transistors are used instead of electronic tubes because they do not require heating. On the contrary, they release heat which is conducted off via the cooling vane. It is a main feature of the device according to the invention that this cooling vane is used as a means for transferring heat to the bottom wall of the treatment part of the casing of the device.

This use, in accordance with the invention, of a power transistor as an electrical heating element, and of its cooling vane as heat transfer means, offer the advantages of very rapid heat supply to the treatment face, which supply depends on the electric current prevailing at a given time, furthermore, of an easily achievable temperature regulation, and of relatively low cost.

On the other hand, the outer shape of the device according to the invention allows it to be held easily in one of the user's hands, and to move its treatment face easily into contact with the skin of the body portion to be treated, in particular of a portion of the patient's face, and to pass the device over the skin of such body portion, regardless of the position of the device in the user's hand, and of the position of the user's hand, in relation to the patient's body.

BRIEF DESCRIPTION OF THE DRAWINGS

Further details of the invention will be described in the accompanying drawings in which.

DETAILED DESCRIPTION OF THE EMBODIMENTS SHOWN IN THE DRAWING

Figure 1:
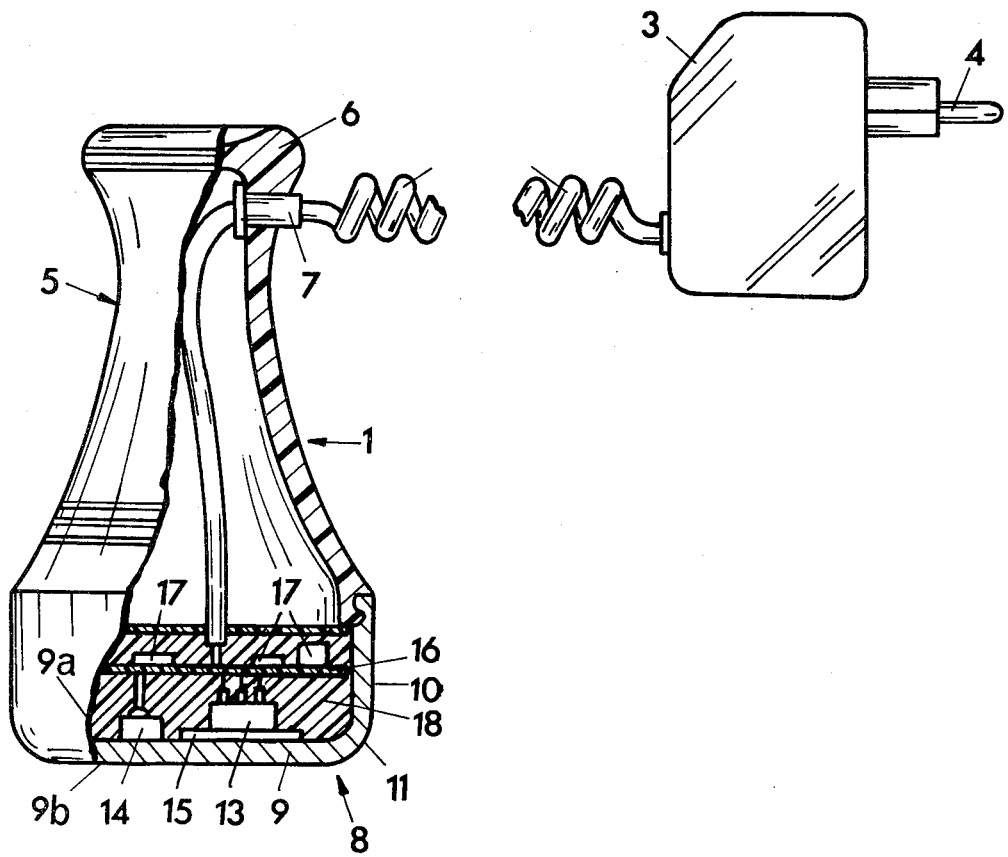
FIG. 1 is a schematic view, partially in axial section, of a preferred embodiment of the hand-held device for local heat treatment of the skin.

As shown in FIG. 1, the casing 1 has a generally pear-shaped configuration with a flattened frontal or lower end and a concavely vaulted neck towards its rear or upper end. The terms "upper" and "lower" refer to the position of the device as shown in the drawings, which is the position in which the hand-held device will be urged downwardly against a horizontally positioned, upwardly facing portion of a patient's skin.

The device 1 is fed with low voltage direct electric current by means of a spring-coiled cable 2 connected to a step-down transformer 3. The latter is equipped with a male plug 4 which can be plugged in a female plug of a city main in a well-known manner. The casting of the device 1 consists of two parts. A handle part 5 has a knob-shaped upper portion 6 which has at its upper end an annular supporting surface, so that the heated device can be placed on this surface in upside down-position when the device is not in use. The cable 2 extends into the interior of handle part 5 via a sleeve 7 which holds it tightly against being pulled out and against sharp bending.

The cross section of the handle part 5 is gradually broadened in downward direction and is detachably connected with a cup-shaped treatment part 8. The latter has a flat bottom wall 9 and a cylindrical sidewall 10 which merges with the bottom wall 9 in a rounded merging zone 11. The handle part 5 is preferably made of synthetic plastic resin material or drawn from metal sheet or a similar material. The treatment part 8 is made from easily cleaned, corrosion-resistant material of good heat conductivity, for instance of chromium steel, eloxated aluminum, chromed or nickel-coated copper or brass or the like. The surface of the treatment part 8 is preferably smooth and optionally polished.

On the inner face 9a of the bottom wall 9 of treatment part 8 there are mounted an electrical heating element 13 and an electrical temperature sensor unit 14 in intimate heat transfer contact with the bottom wall 9, the heating element 13 by lying flat and smooth and airtight, i.e. free from air cushions, against the inner bottom face 9a or being partially inserted into flat recesses in the latter. The heating element 13 is a power transistor whose excess heat, generated by the passage of direct electrical current therethrough is used for heating the bottom wall 9 and sidewall 10 of treatment part 8. The power transistor 13 has a metal hull 13a which is formed integral with a cooling vane 15. The latter serves as a heat-transfer element which is mounted in heat transfer contact on the interior face 9a of bottom wall 9. The heat sensor 14 is preferably a cold conductor the ohmic resistance of which increases with rising temperature. A bimetal feeler or a resistance thermometer with variable equalizing resistor can be used as the heat sensor unit 14. Advantageously, the cold conductor has a reference temperature of about 40° C., a temperature coefficient of from about 15 to 20%/K and a heat-conductivity of at least 30 milliwatt/K.

Above the power transistor 13 and the heat sensor 14 there is provided a small bearing plate 16 of electrically insulating material which plate bears further electrical elements 17, preferably in the form of a printed surface, which constitute a control circuit for the power transistor 13. The ends of the two leads in cable 2 as well as the contact parts of the power transistor 13 and of the cold conductor 14 are affixed to the bearing plate 16. The remaining interior space of the treatment part 8 is preferably filled with poured-in synthetic resin 18 which protects the various elements and the circuit therein from mechanical and chemical attack (humidity) and prevents inspection.

Figure 2:
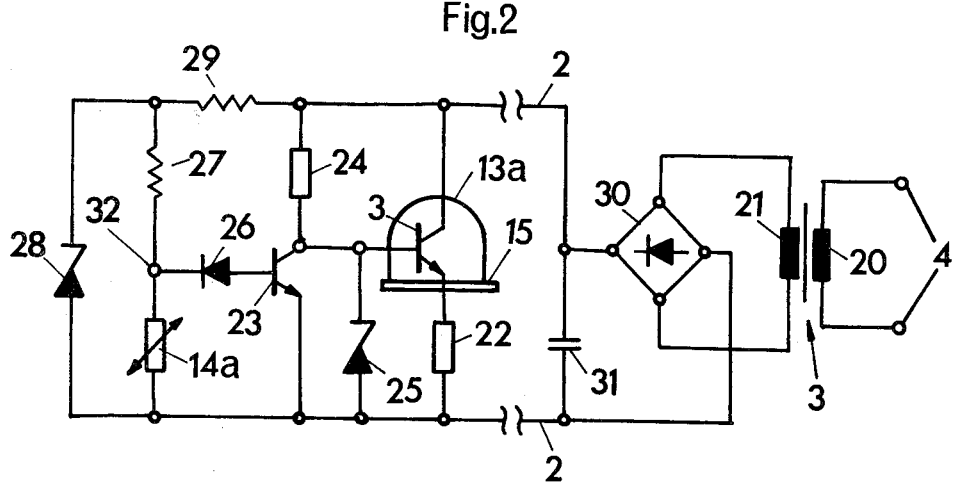
FIG. 2 shows schematically an electronic control circuit of the preferred embodiment shown in FIG. 1.
Figure 3:
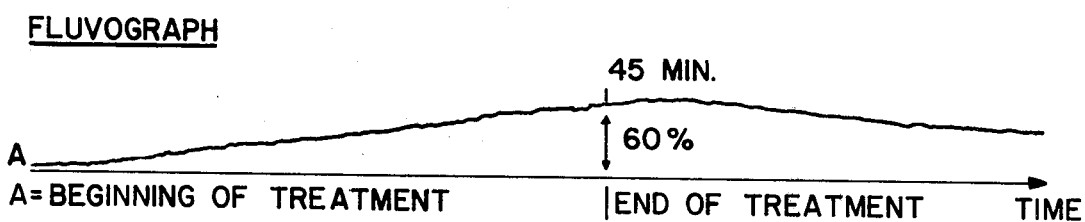
FIG. 3 represents a graph showing a curve plotted with a HENSEL-fluvograph.
Figure 4:
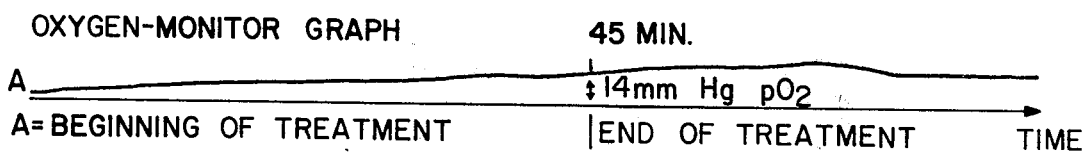
FIG. 4 represents a graph showing a curve taken with an Oxygen-Monitor according to CLARK.
Figure 5:
FIGS. 5 and 6 show thermographs taken of the left profile and of the front, respectively, of the face of a 26-year old woman, before treatment with device illustrated in FIGS. 1 and 2, and FIGS. 7 and 8 show thermographs taken of the left profile and of the front, respectively, of the face of the same woman, after a 45 minute-treatment with the device illustrated in FIGS. 1 and 2.
Figure 6:
Figure 7:
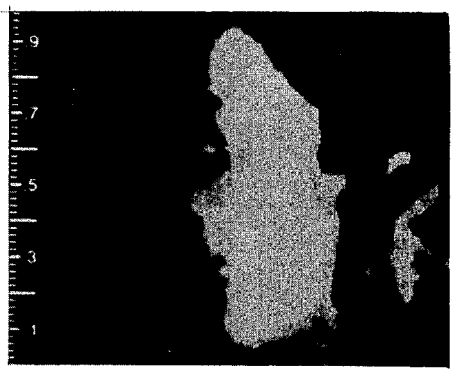
Figure 8:
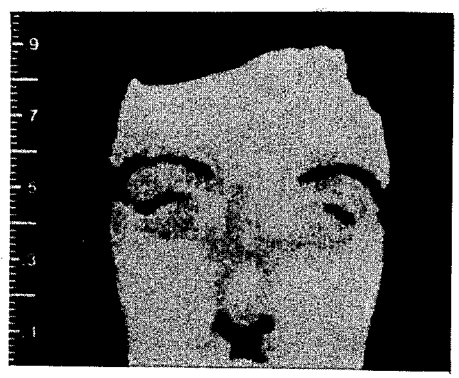

In FIG. 2 there is shown schematically a preferred example of a circuit for operating the device according to the invention and, more in particular, for maintaining a constant temperature of the bottom wall 9. The step-down transformer 3 which is provided with plug pins 4 and with separate windings 20 and 21 reduces the voltage from the main which flows through primary winding 20, to a lower and therefore less dangerous voltage of, for instance, 24 volts, which is delivered from secondary transformer winding 21 to the device 1 via the cable 2. The electrical elements 17 borne by bearing plate 16, the collector 13c and the emitter 13e of the power transistor 13, are supplied with this reduced voltage. The power transistor 13 in this preferred embodiment is an npn-transistor the load of which is determined by the secondary winding 21 of the transformer 3 and by a current-limiting transistor 22 which is interposed in the lead to the emitter 13e. As mentioned previously the excess heat generated by the flow of current through transistor 13 is used for heating the treatment surface, i.e. the external surface 9b of the bottom wall 9 of treatment part 8 (FIG. 1.).

The base 13b of the power transistor 13 is connected, for current control, to the collector 23c of an npn-control transistor 23, the collector resistor 24 and emitter 23e of which are also fed the voltage supplied via the two leads of cable 2. In the base-emitter circuit of power transistor 13 there is provided a Z-diode 25 as voltage-limiting element which limits on the one hand, the positive control voltage at the base of the power transistor 13 to, for example, 12 volts, and which prevents on the other hand, the occurance of a negative voltage of the collector of the control transistor 23. Moreover, this Z-diode 25 provides for a particularly quick response of the power transistor 13 to variations of temperature detected by the heat sensor 14, even if these variations are only minor ones. A conventional rectifying unit is shown at 30.

In order to control the control transistor 23 and to adjust the electrical heating by means of the power transistor 13, the base 23b of the control transistor 23 is connected via a protective diode 26 to a connecting point 32 which is located between a fixed resistor 27 and a variable resistor 14a, connected with one another in series, of a cold conductor serving as a resistance thermometer 14. To this series-connected unit 27,14, there is fed the voltage which lies at a Z-diode 28 which is connected in parallel with the aforesaid series-connected unit 27,14 and which is connected to one of the leads of cable 2 via a resistor 29 and directly to the other lead of cable 2. The Z-diode 28 ensures a quick response of the control transistor 23 to temperature variations.

The Z-diode 28 causes the negative half waves of the alternating voltage at the connecting point 32 of resistors 27 and 29 to be short-circuited, and causes the positive half waves to be limited to a determined value, e.g. to 3.3 volts. Thus, trapeze-shaped positive signals are applied to the base of the control resistor 23, the amplitude of which signals is determined sharply by the voltage division ratio of the resistor 27 and the resistor of heat sensor 14 and correspondingly controls the power resistor 13, i.e. the heat emanated by the latter. When, during use of the device 1, there occurs a cooling of treatment part 8 and therefore of the cold conductor thermometer 14, this causes a decrease of the resistance of the latter. Consequently, there is a rise in voltage at the collector-connected terminal of resistor 24 and this in turn causes the increase of the current flowing through the power transistor 13 and an increase in heat loss of the transistor and of the heat directly transferred to the bottom wall 9 of treatment part 8. The reverse will occur when the device 1 is removed from the heat-absorbing skin with a consequent rise in the temperature of bottom wall 9. The desired temperature to be maintained in bottom wall 9 corresponds to a determined ratio of voltage division between the resistor 27 and the resistor 14a of the heat sensor (cold conduction thermometer) 14. As in particular the resistance value of the cold conductor can vary individually, it may be necessary to equalize the same so that a surface temperature of the bottom wall 9 of, for instance, 40° C. can be maintained. This can be achieved, in manufacturing the device 1, by equalizing the resistor 27 either by means of fixed resistors or by replacing the resistor 27 by a combination of a fixed and a variable resistor. On the other hand, voltage fluctuations in the main do not influence the desired temperature value to be maintained as the voltage at the voltage divider 27,14 is kept sufficiently stable by the Z-diode 28.

The described embodiment can be varied, for instance, by housing the transformer 3 in the interior of handle part 5, and the latter can also be provided with switch means for switching the device 1 on and off. Furthermore, when a more sophisticated device is demanded the device 1 can be equipped with temperature indicating means, for instance, with a mercury thermometer which is particularly sensitive in the operational temperature range about or below 40° C., or a liquid crystal indicator. It is also possible to provide for adjusting means for the desired temperature, e.g. a resistor which is adjustable from the outside and which is connected with resistors 27 (FIG. 2).

An advantage of the hand-held device described above resides in that during operation its treatment surface shows only minor deviations from the desired temperature value, due to the fact that the heat transfer from the used power transformer occurs with very small heat losses thanks to the integrated construction of a heat-generating semiconductor crystal and heat-abducting cooling vane. This could be achieved with use of a conventional heating coil only with considerably more complicated arrangements or not at all. The above-mentioned advantage of only minor deviations from a desired temperature value is further achieved owing to the described electronic circuit arrangement which avoids lags in switching-on and switching-off the heating current, but which rather provides for a continuous supply of half waves of the fed voltage to the power transistor, wherein the current intensity is continuously and infinitely detected depending on the temperature of the treatment surface.

A further essential advantage of the above-described hand-held device according to the invention resides in its external shape which permits particularly easy handling during use. In particular, when heat-treating and massaging the skin of a patient's face, the device permits reaching all inwardly vaulted body areas such as the face portions around the eyes or below the chin in an effective manner without difficulties and without any arduous positioning of the hand holding the device. When using the device regularly alone or together with a facial cream, this affords a better blood flow in the skin and thus a delay of its aging process. A simultaneous application of a facial cream causes no problems owing to the smooth, rounded surface of the treatment part of the device which also permits easy cleaning of the same.

TESTS CHECKING THE EFFECTIVENESS OF APPLYING THE HAND-HELD DEVICE ACCORDING TO THE INVENTION

The influence exercized on blood-flow in the skin by application of the hand-held device according to the invention was checked in tests carried out with a HENSEL fluvograph. Supplementary tests were carried out with an oxygen monitor Type 5.300 manufactured by Bio-Electronics of Roche, Switzerland.

A. Fluvography with the HENSEL-Fluvograph

The HENSEL-fluvography method was used to measure the heat conductivity of the skin of a test person, i.e. a value which is linearly proportional with blood-flow through the skin and can therefore be used to measure the amount of the last-mentioned flow. During measuring, a graphic curve is being continuously recorded which illustrates the amount of blood flow and indicates any influencing of the latter by a corresponding change in the curve. Thus, a rise or drop in the curve and optionally also the amplitude of such variation can be read out, showing a corresponding increase or reduction in the blood flow through the skin.

Test conditions such as room temperature, humidity of the ambient air, avoidance of noise or other disturbances were held constant throughout the tests. These tests were always carried out by the same expert dermatologist at the same time of the day on test persons who had volunteered for the tests.

Transcutaneous oxygen mesurements carried out with an oxygen monitor

These measurements were carried out with a subtle polarographic method, in which the oxygen partial pressure, $p[O_2]$, was measured in the skin with the aid of Clark's oxygen sensor which was fastened on the surface of the skin.

Test arrangement

On the day of testing, the test persons were not allowed to consume beverages containing coffein or alcohol. The test procedure, the apparatus and the application of the measuring heads on their bodies were explained and shown to them before the beginning of the tests in order to avoid any psychic traumatisation. Six persons were tested with the fluvograph and with the oxygen monitor, generating six fluvograph curves and six oxygen-monitor curves.

Results of Fluvograph Tests

Six test persons were subjected to Fluvograph tests carried out with a device according to the invention under uniform conditions for the same period. The six Fluvographs showing, respectively, blood flow through the skin of the different test persons with the result that all test persons showed an increase of blood flow through the tested skin area while the device was being used. The magnitude of the increase was found to be between 11 and 108% relative to the initial blood flow through the skin prior to application of hand-held device. The Fluvograph curves showed that these increases of blood flow through the skin lasted till the end of the application of the device and an improved blood flow through the skin of the treated skin portion lasted for an average of about 30 minutes approximately after the treatment had ceased.

On the basis of a total of twelve tests carried out with the Fluvograph and the Oxygen Monitor, respectively, there was noted an improved blood flow through the skin and also an improved supply of oxygen through the skin. An interesting effect noted was an improved supply of oxygen even after the application of the device according to the invention had ceased; in three of the six test cases oxygen supply after ceasing use of the device was even larger. It could not be determined when the improvement of the oxygen supply of the treated skin portion ended as the tests had to be terminated 47 minutes after cessation of use of the device. At that time, the oxygen supply was still at an increased level.

A 26-year old woman was treated with the device according to the invention and Fluvographs were taken before and after treatment. These show a significantly improved increase of blood flow through the skin after treatment.

Testing device: AGA Thermovision Medical.

I claim:

1. A hand-held device for the local heat treatment of a patient's skin which device comprises:
   (a) a casing having a bottom wall the outer face of which contains a treatment face;
   (b) a handle part which is connected to the casing at a part thereof spaced from the bottom wall of the latter; as well as
   (c) an electric heating unit in the interior of the casing which unit comprises
   (i) a power transistor, a cooling vane and a heat sensor unit adapted for measuring the temperature of the treatment face;
   said power transistor comprising an encapsulating hull being of heat-conductive material and being integral with said cooling vane, and said cooling vane being of a flat configuration and in planar contact with the inner surface of said bottom wall;

and the heat sensor unit being arranged spaced from said cooling vane on the inner surface of the bottom wall of the casing in direct physical contact with said bottom wall; and (ii) an electric circuit means disposed in the interior of the casing which circuit means is adapted for controlling electric current flow in the power transistor in response to any temperature variations of the treatment face of the bottom wall detected by said heat sensor unit, said electric circuit means being connected with the power transistor and the heat sensor unit, and comprising connecting means adapted for connecting said circuit means with a source of low voltage direct current, and a poured-in synthetic resin filling in the lower part of said casing, embedding said power transistor, cooling vane and electric circuit means and filling the space between said cooling vane and said heat sensor unit.

2. The device of claim 1, wherein said heat sensor unit comprises a cold conductor as heat sensor and a variable resistor associated with said cold conductor.

3. The device of claim 1, wherein the heat sensor unit comprises a resistance thermometer consisting essentially of a measuring resistor and a variable voltage-equalizing resistor.

4. The device of claim 1, wherein said electrical circuit means comprises a bearing plate of electrically insulating material, having an upper surface and an underside and a printed circuit on said plate, said bearing plate being located in said casing spaced from said bottom wall at a distance above said hull of said power transistor and above said heat sensor unit and bearing on said bearing plate upper surface the remaining elements of said electric circuit means.

* * * * *